United States Patent
Liu

(10) Patent No.: US 6,893,418 B2
(45) Date of Patent: *May 17, 2005

(54) DRAINAGE CATHETER WITH DILATING MEMBER

(75) Inventor: Clifford M. Liu, Randolph, MA (US)

(73) Assignee: Boston Scientific SciMed, Inc., Maple Grove, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 10/375,488

(22) Filed: Feb. 27, 2003

(65) Prior Publication Data

US 2003/0144636 A1 Jul. 31, 2003

Related U.S. Application Data

(63) Continuation of application No. 09/755,588, filed on Jan. 5, 2001, now Pat. No. 6,547,761.
(60) Provisional application No. 60/174,885, filed on Jan. 7, 2000, and provisional application No. 60/195,931, filed on Apr. 10, 2000.

(51) Int. Cl.[7] ............................................. A61M 29/00
(52) U.S. Cl. ..................................................... 604/106
(58) Field of Search .......................... 604/509, 95.04, 604/104–109, 164.03, 164.04, 127, 540

(56) References Cited

U.S. PATENT DOCUMENTS

| | | | |
|---|---|---|---|
| 3,108,593 A | 10/1963 | Glassman | |
| 3,241,554 A | 3/1966 | Coanda | |
| 3,261,357 A | 7/1966 | Roberts et al. | |
| 3,490,457 A | 1/1970 | Petersen | |
| 3,713,447 A | 1/1973 | Adair | |
| 3,815,608 A | * 6/1974 | Spinosa et al. | 604/105 |
| 3,860,006 A | 1/1975 | Patel | |
| 3,938,530 A | 2/1976 | Santomieri | |

(Continued)

FOREIGN PATENT DOCUMENTS

| | | |
|---|---|---|
| EP | 0 234 364 A2 | 9/1987 |
| EP | 0 365 269 B1 | 4/1990 |
| EP | 0 368 473 A2 | 5/1990 |
| EP | 0 513 198 B1 | 11/1992 |
| EP | 0 516 189 B1 | 12/1992 |
| EP | 0 523 176 B1 | 1/1993 |
| EP | 0 605 427 B1 | 7/1994 |
| EP | 0 609 020 A1 | 8/1994 |
| GB | 688450 | 3/1953 |
| GB | 955490 | 4/1964 |
| GB | 1014570 | 12/1965 |
| GB | 1046478 | 10/1966 |
| GB | 1463269 | 2/1977 |
| WO | WO 98/44980 | 10/1998 |
| WO | WO 99/16355 | 4/1999 |

*Primary Examiner*—Larry I. Schwartz
*Assistant Examiner*—Michael G. Bogart
(74) *Attorney, Agent, or Firm*—Edwards & Angell, LLP

(57) ABSTRACT

A medical device for draining fluid from the body of a patient comprises an elongate member that defines a lumen and includes a proximal end and a distal portion. The device further comprises a dilating member disposed in the distal portion of the elongate member. The dilating member comprises a plurality of arms movable from a collapsed state to an expanded state in which the arms protrude radially to anchor the device within the body of the patient. The device includes a tension member that extends through the lumen to the dilating member and couples to the plurality of arms. Application of tension to the tension member causes the arms to move to the collapsed state thereby permitting insertion and removal of the device into and from the body of the patient. Some embodiments include a tension control member disposed at the proximal end of the elongate member and movable in at least a first direction and a second direction to increase and decrease tension to one or more tension members.

16 Claims, 14 Drawing Sheets

U.S. PATENT DOCUMENTS

| | | | |
|---|---|---|---|
| 3,946,741 | A | 3/1976 | Adair |
| 4,043,346 | A | 8/1977 | Mobley et al. |
| 4,284,081 | A | 8/1981 | Kasper et al. |
| 4,299,225 | A | 11/1981 | Glassman |
| 4,337,775 | A | 7/1982 | Cook et al. |
| 4,349,029 | A | 9/1982 | Mott |
| 4,350,161 | A | 9/1982 | Davis, Jr. |
| 4,361,152 | A | 11/1982 | Patel |
| 4,372,313 | A | 2/1983 | Villari et al. |
| 4,393,873 | A | 7/1983 | Nawash et al. |
| 4,405,163 | A | 9/1983 | Voges et al. |
| 4,432,757 | A | 2/1984 | Davis, Jr. |
| 4,474,569 | A | 10/1984 | Newkirk |
| 4,543,100 | A | 9/1985 | Brodsky |
| 4,555,242 | A | 11/1985 | Saudagar |
| 4,572,186 | A | 2/1986 | Gould et al. |
| 4,600,402 | A | 7/1986 | Rosenberg |
| 4,601,713 | A | 7/1986 | Fuqua |
| 4,610,663 | A | 9/1986 | Rosenberg |
| 4,627,838 | A | 12/1986 | Cross et al. |
| 4,655,771 | A | 4/1987 | Wallsten |
| 4,666,433 | A | 5/1987 | Parks |
| 4,699,611 | A | 10/1987 | Bowden |
| 4,701,163 | A | 10/1987 | Parks |
| 4,705,502 | A | 11/1987 | Patel |
| 4,740,195 | A | 4/1988 | Lanciano |
| 4,758,219 | A | 7/1988 | Sacks et al. |
| 4,807,626 | A | 2/1989 | McGirr |
| 4,808,163 | A | 2/1989 | Laub |
| 4,861,334 | A | 8/1989 | Nawaz |
| 4,878,893 | A | 11/1989 | Chin |
| 4,921,484 | A | 5/1990 | Hillstead |
| 4,954,126 | A | 9/1990 | Wallsten |
| 4,973,301 | A | 11/1990 | Nissenkorn |
| 4,995,868 | A | 2/1991 | Brazier |
| 5,041,085 | A | 8/1991 | Osborne et al. |
| 5,135,517 | A | 8/1992 | McCoy |
| 5,176,626 | A | 1/1993 | Soehendra |
| 5,192,286 | A | 3/1993 | Phan et al. |
| 5,203,773 | A | 4/1993 | Green |
| 5,217,451 | A | 6/1993 | Freitas |
| 5,257,975 | A | 11/1993 | Foshee |
| 5,273,529 | A | 12/1993 | Idowu |
| 5,290,249 | A | 3/1994 | Foster et al. |
| 5,339,803 | A * | 8/1994 | Mayzels et al. ............ 600/201 |
| 5,403,324 | A | 4/1995 | Ciervo et al. |
| 5,409,460 | A | 4/1995 | Krumme |
| 5,419,764 | A | 5/1995 | Roll |
| 5,441,485 | A | 8/1995 | Peters |
| 5,454,365 | A | 10/1995 | Bonutti |
| 5,454,790 | A | 10/1995 | Dubrul |
| 5,514,112 | A | 5/1996 | Chu et al. |
| 5,514,156 | A * | 5/1996 | Schulze et al. ............ 606/205 |
| 5,749,826 | A | 5/1998 | Faulkner |
| 5,876,417 | A | 3/1999 | Devonec et al. |
| 5,928,208 | A | 7/1999 | Chu et al. |
| 5,957,900 | A | 9/1999 | Ouchi |
| 5,971,950 | A | 10/1999 | Lopez et al. |
| 5,984,957 | A | 11/1999 | Laptewicz et al. |
| 5,989,241 | A | 11/1999 | Plishka et al. |
| 6,086,556 | A | 7/2000 | Hamilton et al. |
| 6,210,370 | B1 * | 4/2001 | Chi-Sing et al. ........ 604/164.03 |
| 6,547,761 | B2 * | 4/2003 | Liu ........................... 604/104 |
| 6,638,247 | B1 * | 10/2003 | Selmon et al. ............. 604/104 |
| 6,652,505 | B1 * | 11/2003 | Tsugita ....................... 604/509 |

* cited by examiner

LOCKED

UNLOCKED

DRAINAGE CATHETER WITH DILATING MEMBER

CROSS-REFERENCE TO RELATED CASES

This application is a continuation of U.S. patent application Ser. No. 09/755,588, now U.S. Pat. No. 6,547,761, filed Jan. 5, 2001, which claims the benefit of and priority to provisional U.S. patent application Ser. No. 60/174,885, filed Jan. 7, 2000, and provisional U.S. patent application Ser. No. 60/195,931, filed Apr. 10, 2000.

TECHNICAL FIELD

The invention relates to medical catheters, and, more particularly, to drainage catheters with distal anchoring mechanisms.

BACKGROUND INFORMATION

Some medical treatments involve the use of a medical catheter with a distal anchor that retains the catheter in position in the body of a patient. Some treatments use a drainage catheter. For example, procedures for the suprapubic catheterization of the bladder drain the bladder after surgery or when an obstruction plugs the genitourinary system. Percutaneously inserted catheters can also drain the kidneys, biliary system, abscesses, other sites of fluid collection and other viscera. As an alternative to providing drainage, percutaneously inserted catheters can introduce substances into the patient's body such a fluids introduced through gastrostomy feeding tubes.

Since body movements can inadvertently lead to catheter displacement, various anchoring mechanisms have been developed. For example, a Foley bladder catheter includes an inflatable balloon at the distal end, an inflation channel in the walls of the catheter, an external supply of inflation fluid connected to the channel and a valve to keep the fluid in place and the balloon inflated.

Alternatively, the distal end of the catheter can include a "pigtail loop" formed from a flexible tube. Typically, the pigtail loop is preformed from a shape-memory material. For introduction into a patient, a physician inserts a stiff cannula or stylet into the catheter lumen to straighten the pigtail loop. The distal end of the flexible tube returns to the pigtail configuration after the physician removes the cannula. In some cases, return to the pigtail configuration may be aided or secured by the use of a suture thread that extends through draw ports at two spaced positions on the flexible tube. These draw ports move toward each other when the physician removes the cannula. The physician can then take up slack and secure the pigtail by applying tension to the suture thread. To remove the catheter, the physician can reverse the above procedures.

Other anchor mechanisms include malecots with "wings" or "arms" in a distal portion of the catheter wall. The application of force to a distal tip of the catheter can expand the wings, and the wings extend outward protruding radially to create an anchor for the catheter. The force can be applied by pulling on a suture string or a rod extending through the lumen of the catheter. Alternatively, the wings of the malecot can be formed from a shape-memory material with a naturally protruding configuration, and a stylet is used to push the distal end of the catheter and collapse the malecot.

SUMMARY OF THE INVENTION

A catheter according to the invention does not require the use of a shape-memory material, a stylet, or dual tubes for collapsing an anchor mechanism. Also, catheters according to the invention do not require a physician to manipulate separately two different tension members (e.g., two sutures) extending through the catheter lumen.

A catheter of the present invention includes one or more tension members to pull on one or more arms of a dilating member to collapse the dilating member. The tension members, in cooperation with a lock member, can secure the dilating member in a collapsed state. A single tension control member (located, for example, at the proximal end of the catheter), and operable with one hand, can simultaneously produce opposite changes in tension in two tension members attached to a dilating member.

Catheters according to the invention do not require stylets. A physician can collapse and secure the dilating member, for insertion or removal of the catheter, by applying tension (e.g., a pulling force) to a tension member. Further, catheters of the invention can include a tension control member that cooperatively controls the tension in two separate tension members to permit a physician securely and controllably to expand and collapse the dilating member with the use of just one hand.

In general, in one aspect, the invention features a medical device for draining fluid from the body of a patient. The device comprises an elongate member that defines a lumen and includes a proximal end and a distal portion. The device further comprises a dilating member disposed in the distal portion of the elongate member. The dilating member comprises a plurality of arms movable from a collapsed state to an expanded state in which the arms protrude radially to anchor the device within the body of the patient. The device further comprises a tension member extending through the lumen to the dilating member and coupled to the plurality of arms such that the application of tension to the tension member causes the arms to move to the collapsed state thereby permitting insertion and removal of the device into and from the body of the patient.

Embodiments of this aspect of the invention can include the following features. The device can include a second tension member extending through the lumen to the dilating member. The second tension member couples to a distal end of at least one of the arms such that application of tension to the second tension member causes the arms to move to the expanded state.

The device can further include a tension control member disposed at the proximal end of the elongate member, movable in at least a first direction and a second direction. The tension control member is coupled to the tension members such that movement of the tension control member in the first direction causes an increase in tension of the tension member and a decrease in tension of the second tension member that causes the arms to move to the collapsed state. Movement of the tension control member in the second direction causes an increase in tension of the second tension member and a decrease in tension of the tension member that causes the arms to move to the expanded state.

In some embodiments, the tension members comprise a flexible material. In some embodiments, the tension control member is slidably coupled to the elongate member to permit movement in proximal and distal directions. In other embodiments, the tension control member is rotatably coupled to the elongate member to permit clockwise and counterclockwise rotational movement around a longitudinal axis of the elongate member. In some embodiments, the tension control member is lockable to fix the tensions in the tension members to secure the arms when in the collapsed state, and when in the expanded state.

In general, in another aspect, the invention features a device with a tension control member that cooperatively adjusts the tension in at least two tension members. The device comprises an elongate member that defines a lumen and includes a proximal end and a distal portion. A tension control member is disposed at the proximal end of the elongate member and movable in at least a first direction and a second direction. A first tension member couples to the tension control member at a first site and extends through the lumen to the distal portion. A second tension member couples to the tension control member at a second site and extends through the lumen to the distal portion.

Movement of the tension control member in the first direction causes an increase in tension of the first tension member and a decrease in tension of the second tension member. Conversely, movement of the tension control member in the second direction causes an increase in tension of the second tension member and a decrease in tension of the first tension member.

Embodiments of this aspect of the invention can include the following features. The first and second tension members can comprise a flexible material. The tension control member can be slidably coupled to the elongate member to permit movement in proximal and distal directions. In other embodiments, the tension control member is rotatably coupled to the elongate member to permit clockwise and counterclockwise rotational movement around a longitudinal axis of the elongate member.

The foregoing and other objects, aspects, features, and advantages of the invention will become more apparent from the following description and from the claims.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 2 is an enlarged view of the arm "A" of FIG. 1a.

FIG. 10b is a cross-sectional view that corresponds to FIG. 10a.

DESCRIPTION

Figure 1A:
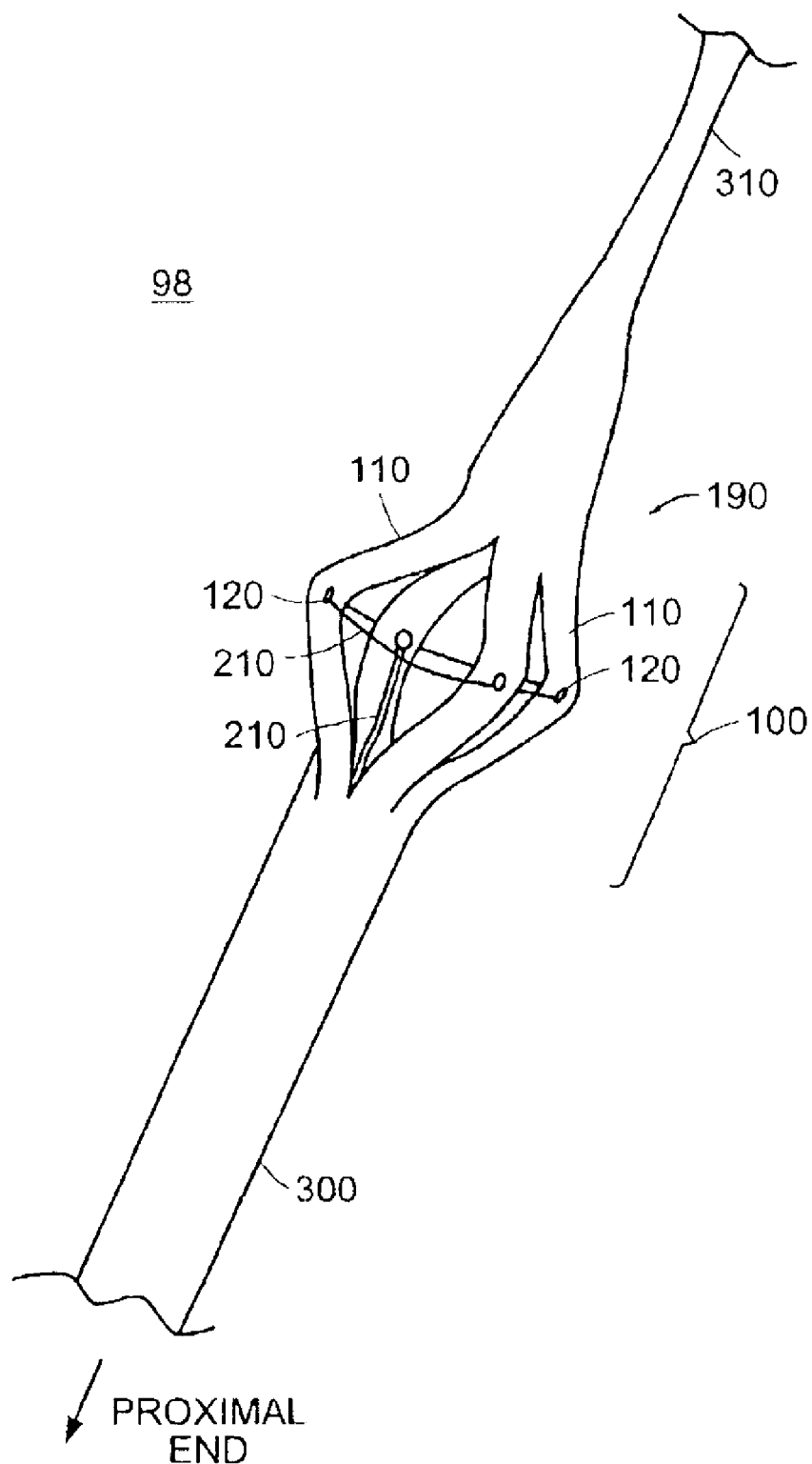
FIG. 1a is a three-dimensional view of the distal portion of an embodiment of a drainage catheter according to the invention.

Referring to FIG. 1a, a physician can use a medical device 98 according to the invention for draining fluid or removing other materials from the body of a patient (the term "physician" is here understood to refer generally to any medical worker). For example, the device 98 can be employed as a catheter for multi-stage percutaneous stone removal or nephrostomy drainage. Other uses include, for example, insertion of the device into a patient for drainage of the bladder, the kidneys, the biliary system, abscesses, other sites of fluid collection and other viscera. As an alternative to providing drainage, percutaneously inserted catheters can introduce substances into the patient's body, such as fluids introduced through gastrostomy feeding tubes.

Figure 6A:
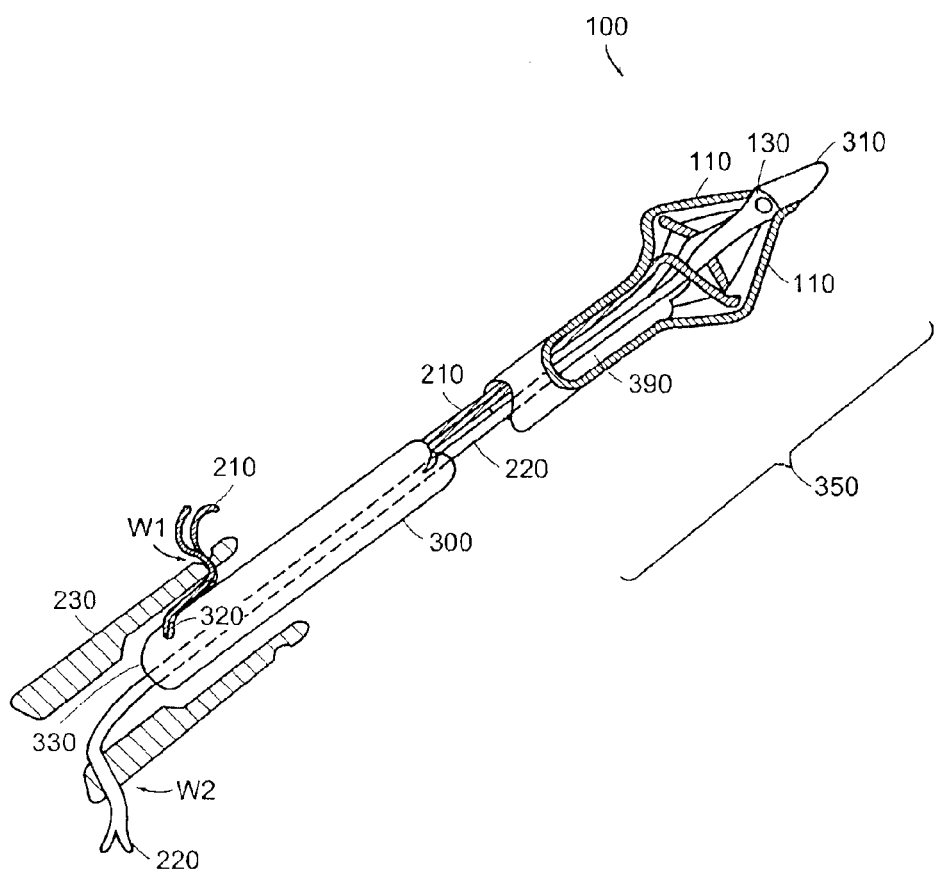
FIG. 6a is a cutaway view of an embodiment of a drainage catheter according to the invention that includes two tension members a slidable tension control member.

The device 98 comprises a dilating member 100 disposed in a distal portion 350 of an elongate member 300 (see also FIG. 6a). The elongate member 300 (partially shown) defines at least one internal lumen 390 (see FIG. 6a) for transporting bodily fluid, and the elongate member 300 includes a proximal end 330 (see FIG. 6a) and the distal portion 350.

Optionally, the elongate member 300 further comprises a distal extension 310 adjacent to a distal end 190 of the dilating member 100. Other embodiments include no extension (see FIG. 4). Use of a distal extension 310 varies with the medical application. For example, the distal extension 310 can be inserted in the ureter to capture urine flow. Alternatively, the dilating portion of a catheter without an extension can reside inside a kidney to directly drain the kidney.

Figure 1B:
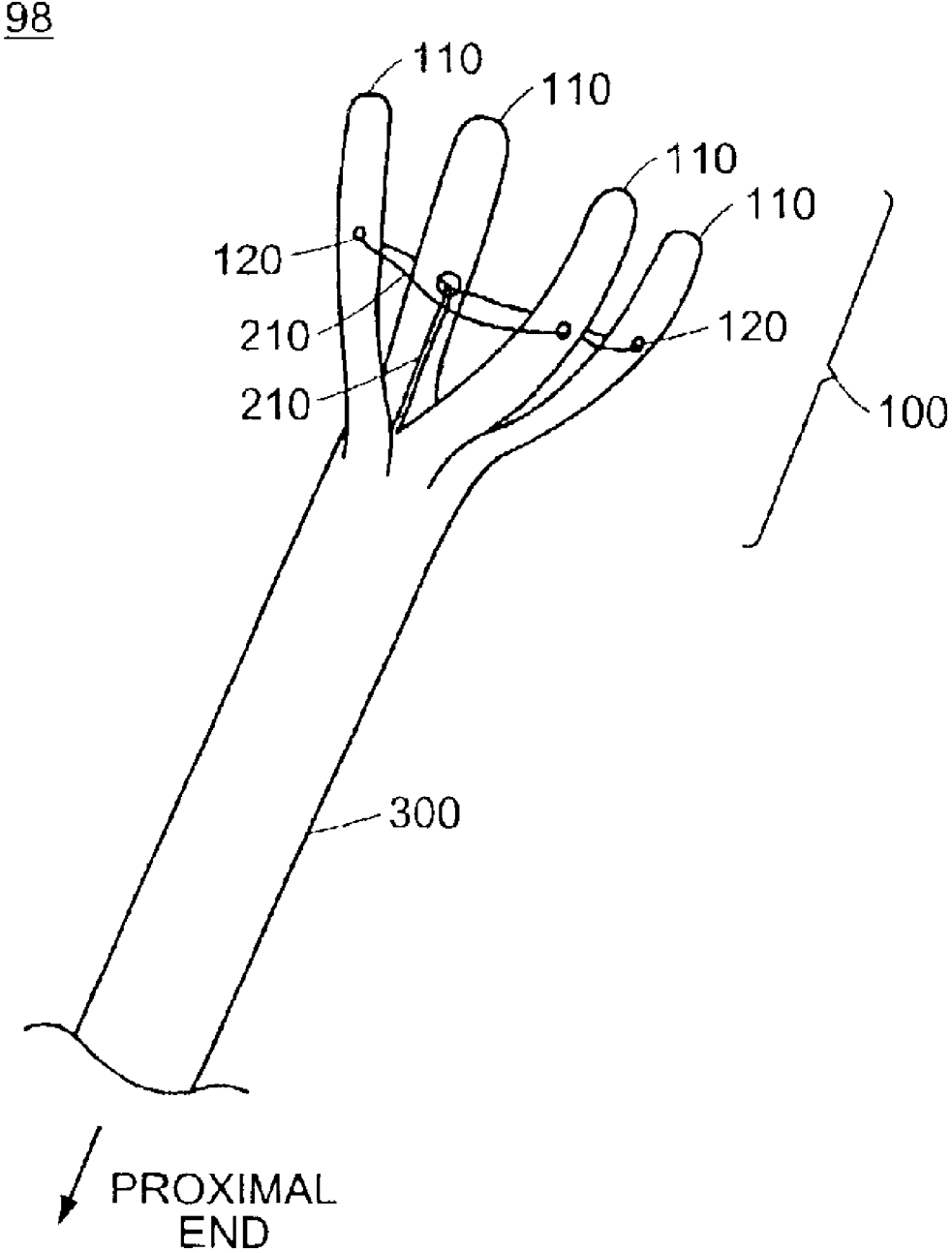
FIG. 1b is a three-dimensional view of the distal portion of an embodiment of a drainage catheter according to the invention.

The dilating member 100 comprises one or more arms 110. In the embodiment depicted in FIG. 1a, the dilating member has four arms 110. Flexing or extending the arms 110 respectively serves to configure the dilating member 100 in an expanded state, i.e. bent arms, or a contracted state, i.e. straight arms 110. When in the collapsed state, a physician can insert the distal portion 350 of the elongate member 300 and the dilating member 100 into an orifice or incision in a patient. When in the expanded state, the dilating member 100 anchors the medical device 98 in the body of the patient. Referring to FIG. 1b, another embodiment of the dilating member 100 comprises one or more curving arms 110 that each are free at one end.

As shown in the embodiment depicted in FIG. 1a, arms 110 can be fabricated by making slits in an elongate member 300 formed from a tube. In general, any suitable flexible, bio-compatible material can serve for tubing. For example, the tubing can comprise a polymer, such as silicone, rubber, polyurethane, pebax or other thermoplastic material. Alternatively, one can bendably attach arms 110 to the elongate member 300, for example via hinges.

In the embodiment depicted in FIG. 1a, the dilating member 100 is formed in a naturally open state, for example using a thermoplastic material. A physician can collapse the dilating member 100 by application of tension to a tension member 210. Application of tension to the tension member 210 causes the arms 110 to extend, i.e. straighten, and move towards each other.

The tension member 210 can comprise a flexible material. Some embodiments use suture thread or other bio-compatible threads. In the embodiment of FIG. 1a, a single thread extends through eyelets 120 in the apex of the curve of the arms 110, while the two ends of the thread extend from one of the eyelets 120 along the lumen 390 to the proximal end 330 of the elongate member 300. Application of tension to the two ends of the thread at the proximal end 330 of the elongate member 300 causes the thread to tighten where it loops through the arms 110, and draws the arms 110 together.

Figure 2:
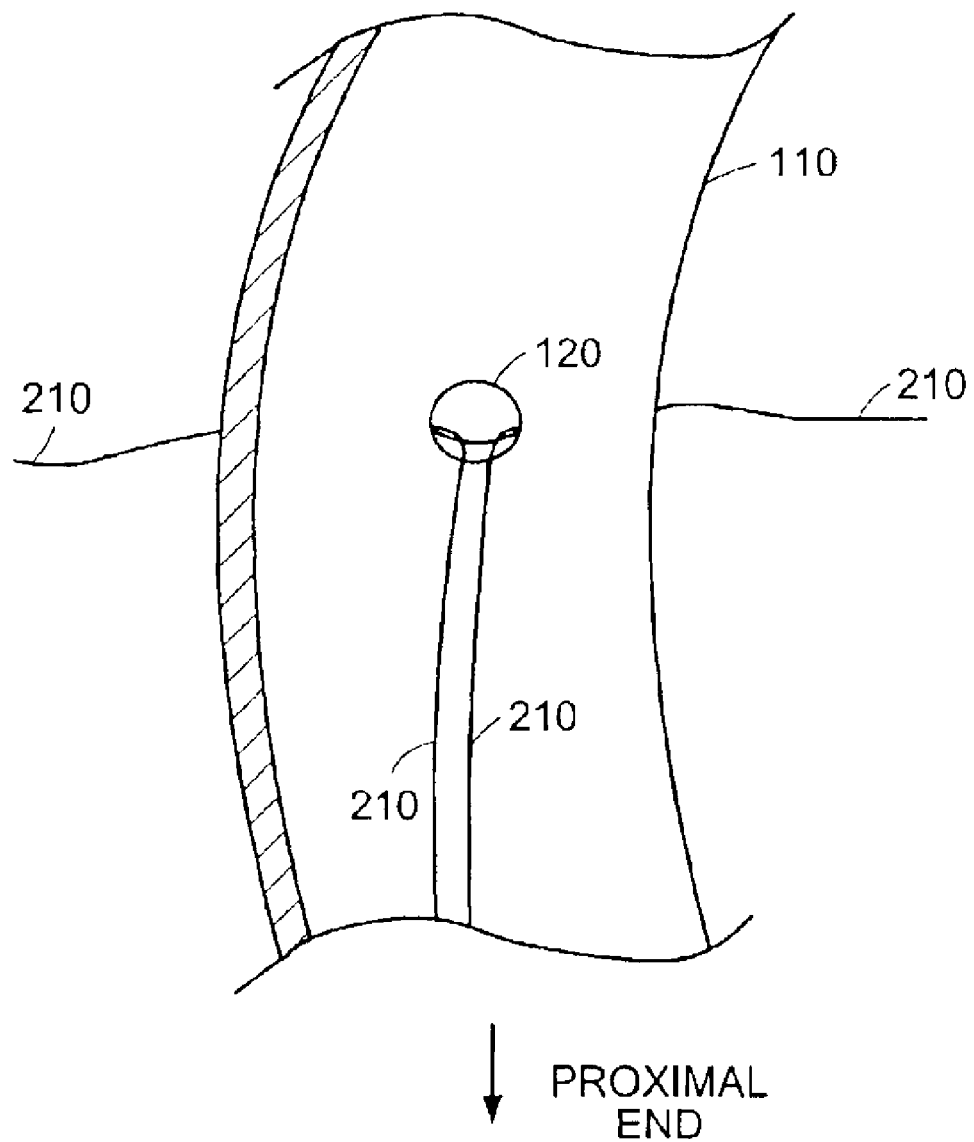

Referring to FIG. 2, the arm 110, labeled A in FIG. 1a, is shown in more detail. The two ends of the thread pass from the outer surface of the arm 210 through the eyelet 120, and extend along the lumen 390 to the proximal end 330 of the elongate member 300. Hence, in the embodiment depicted in FIG. 1, this arm is threaded differently from the remaining arms 210.

In other embodiments, only one end of the thread extends through the lumen 390 to the proximal end 330 of the elongate member 300. The other end of the thread can terminate at various alternative locations. For example, the latter end can couple to the remainder of the thread or to one of the arms 110.

In other embodiments, alternative thread configurations serve as the tension member 210. For example, separate threads can extend to each arm 110 or a single thread can branch to each arm 110 after extending distally through the lumen 390. Another embodiment employs more rigid, linked materials to form the tension member. For example, the tension member 210 can comprise a chain or bendably linked rods.

In another embodiment, all arms 110 are threaded by a common closed loop of thread through each eyelet 120 in each arm 110, and an additional section of thread attaches to the loop and extends along the lumen 390 to the proximal end 330 of the elongate member 300. Alternative embodiments utilize other threading configurations that still serve to pull the arms 110 towards each other when a physician applies tension to one or more thread ends at the proximal end of the catheter.

Figure 3A:
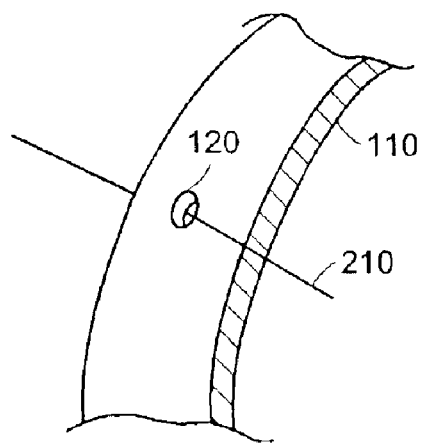
FIG. 3a–c are three-dimensional views of three embodiments of a dilating member arm.

Referring to FIG. 3a, the threading of the three other arms 110 corresponding to the embodiment of FIG. 1a is illustrated. Each arm 110 possesses a centrally located eyelet 120. The tension member 210 passes through the eyelet 120 and continues in either direction to neighboring arms 110. One can vary the direction of threading of the tension member 210 through the eyelets 120 in the arms 110. For example, the tension member 210 can pass from neighbor to neighbor, or can pass directly between non-neighbor arms 110. Further, as the tension member 210 passes through the eyelet 120 on a particular arm 110, the tension member can pass from the inner or outer surface of the arm 110.

Figure 3B:
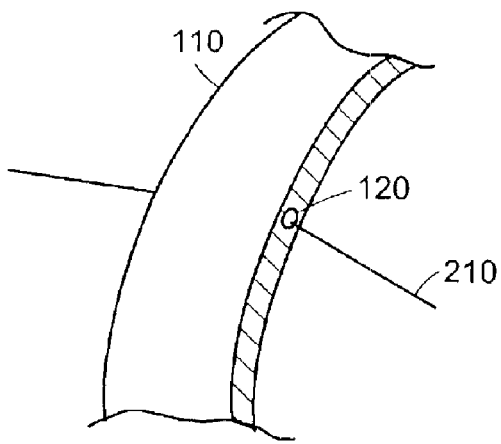
Figure 3C:
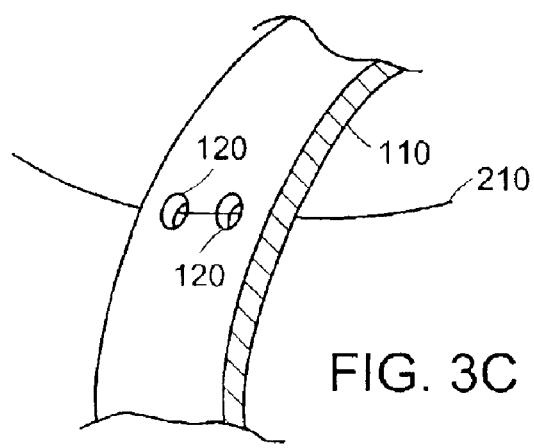

Referring to FIG. 3b and FIG. 3c, other embodiments have different numbers or different locations of eyelets 120 in the arms 110. As illustrated by FIG. 3b, the eyelet 120 can extend laterally through the arm 110. As illustrated by FIG. 3c, the arm 110 can have two or more eyelets. One can satisfactorily employ other eyelet positions and threading configurations for collapsing of the dilating member 100.

Figure 4:
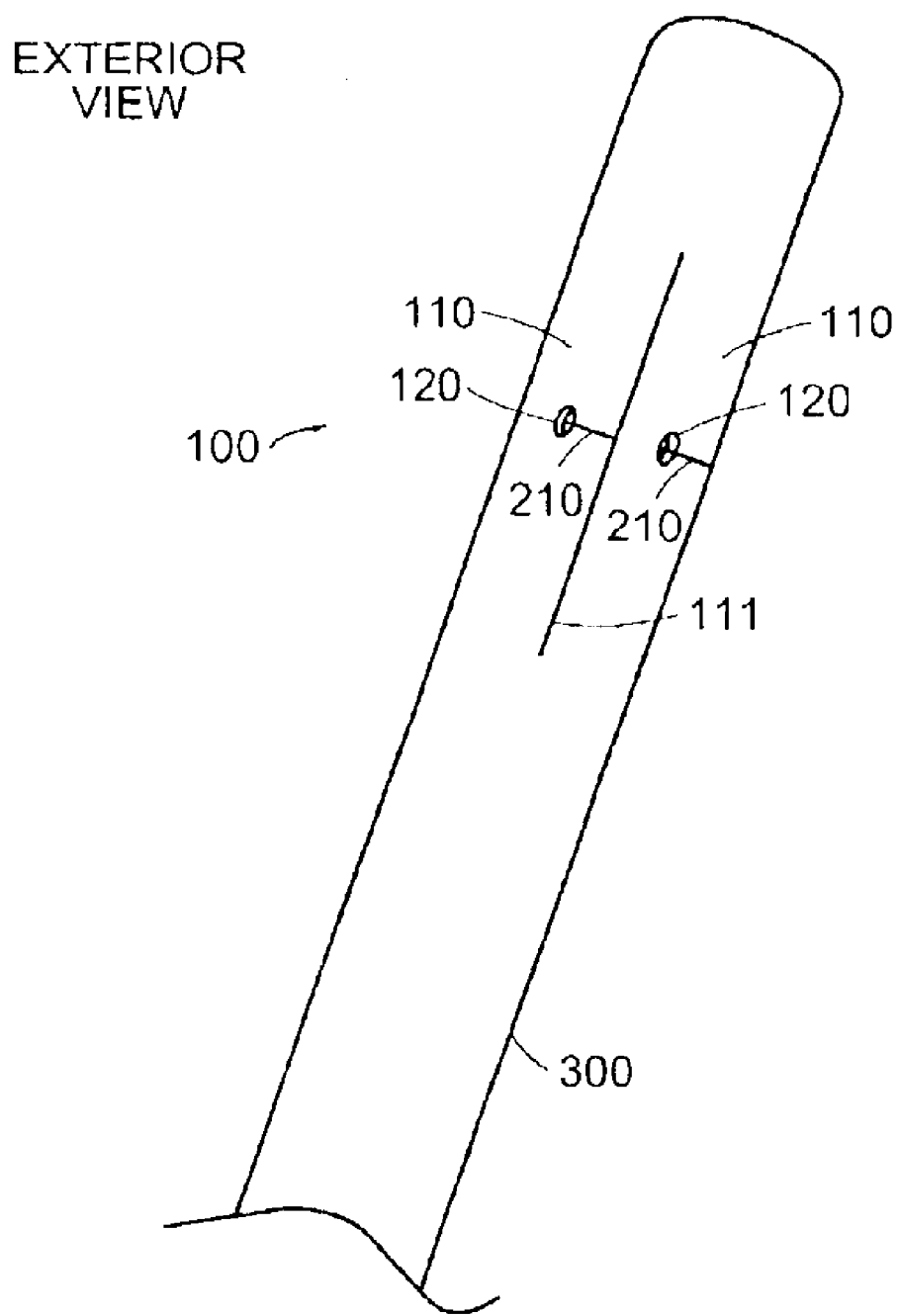
FIG. 4 is a side view of the exterior of an embodiment of a dilating member in a collapsed state.

Referring to FIG. 4, an embodiment of a distal portion 350 of an elongate member 300 with a dilating member 100 in the collapsed state is illustrated. This embodiment corresponds to the embodiment depicted in FIG. 1a. In this collapsed configuration, a physician can readily insert the catheter in, or remove it from, a body cavity. Two arms 110 are visible in this view. These arms 110 touch along slit 111 while in the collapsed state. A tension member 210 made from suture thread (partially visible) passes along the outer surfaces of the arms 110.

Figure 5:
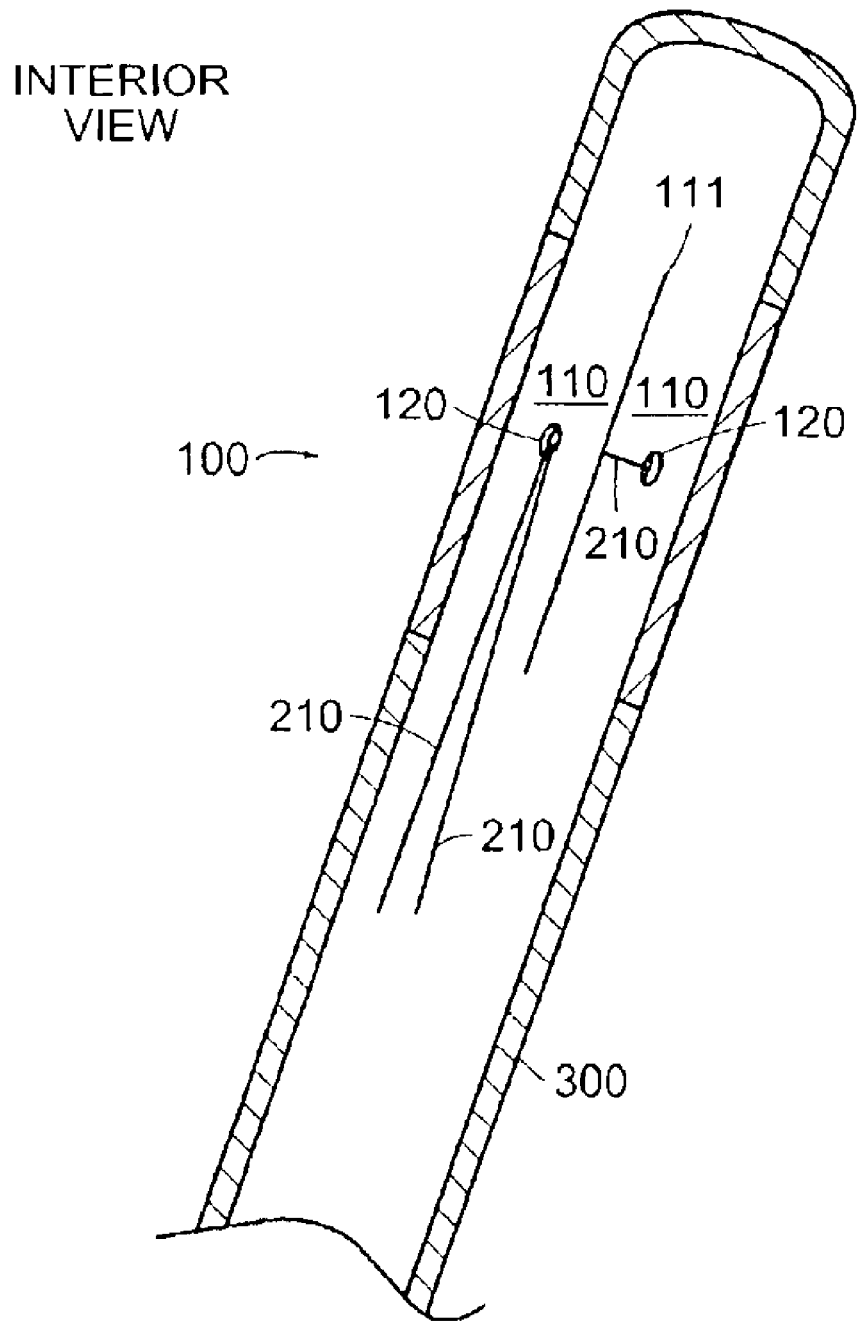
FIG. 5 is a cutaway interior view that corresponds to FIG. 4.

Referring to FIG. 5, a cut-away interior view corresponding to the embodiment of FIG. 4 is shown. Portions of the thread tension member 210 can be seen passing laterally along a portion of the inner surface of one arm 110, and extending towards the proximal end along the inner surface of another arm 110. As described above, pulling on the proximal ends of the thread collapses the arms 110, and holds the arms 110 in the collapsed configuration for insertion or removal of the catheter.

Referring to FIG. 6a, another embodiment of a catheter is illustrated. The catheter includes a second tension member 220. Application of tension to the second tension member 220 causes the dilating member 100 to move to the expanded state. The second tension member 220 can comprise a flexible material. In some embodiments, the second tension member 220 comprises the same material as the tension member 210. The second tension member 220 couples to one of the arms 110. The coupling can be direct, at the distal end 130 of the arms 110 as shown in FIG. 6a, or indirect, for example by attachment to the extension 310 of the distal end of the elongate member 300.

Cooperative releasing and applying of tension to the tension members 210, 220 causes the dilating member 100 to either expand or collapse. To better control such tension, the embodiment depicted in FIG. 6a includes a tension control member 230. The tension control member 230 is disposed at the proximal end of the elongate member 300. In this embodiment, the tension control member 230 comprises a tubular section of material, for example, made from a polymer or a metal. In this embodiment, the tension control member 230 is slidably coupled to the elongate member 300. A physician can slide the tension control member 230 in either direction parallel to the longitudinal axis of the elongate member 300.

The tension members 210, 220 couple to the tension control member 230. The couplings are configured so that the tension in one of the tension members 210, 220 increases while tension in the other tension member 210, 220 decreases upon motion of the tension control member 230 in one of two directions. In the embodiment depicted in FIG. 6a, the tension member 210 extends in a distal direction exterior to the elongate member 300 after exiting the lumen 390 and before attaching to the tension control member 230 (indicated at site "W1"); conversely, the second tension member 220 extends in a proximal direction after exiting the lumen 390 and before attaching to the tension control member 230 (indicated at site "W2"). Attachment can be achieved, for example, by friction or an adhesive.

Sliding the tension control member 230 in a proximal direction causes a pull on the second tension member 220 and a relaxation of the pull on the tension member 210, thus expanding the dilating member 100. Conversely, sliding the tension control member 230 in a distal direction causes a pull on the tension member 210 and a relaxation of the pull on the second tension member 220, thus collapsing the dilating member 100.

Figure 6B:
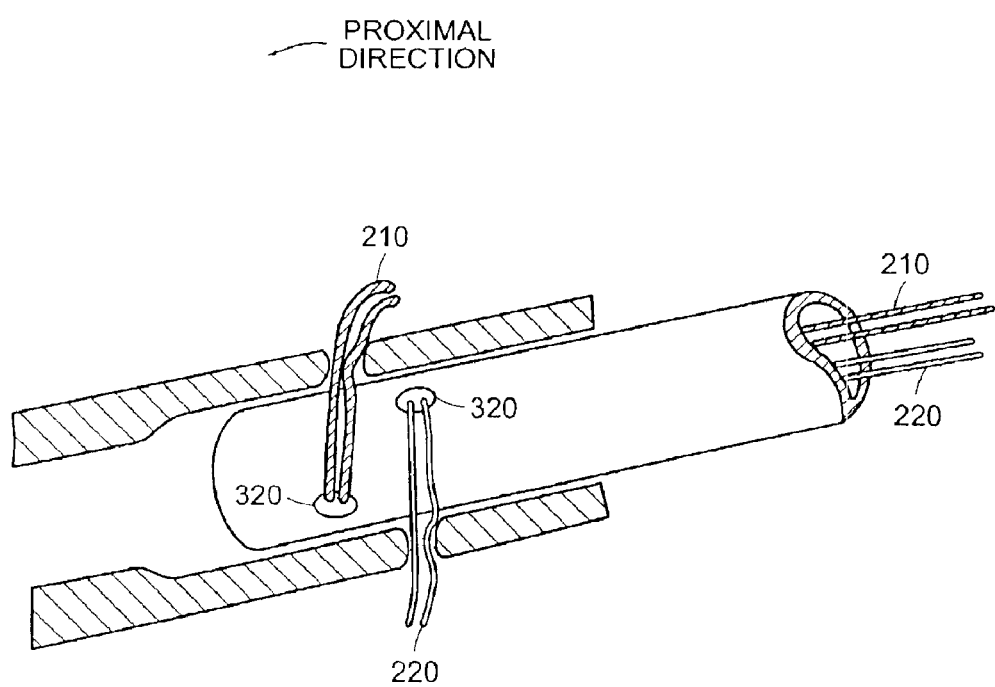
FIG. 6b is a cutaway view of an embodiment of a rotatable tension control member.

Referring to FIG. 6b, another embodiment of a tension control member 210 permits adjustment of tension in one or more threads by rotational movements. In the embodiment depicted in FIG. 6b, the tension member 210 extends in a counterclockwise (when looking towards the distal end of the catheter) direction exterior to the elongate member 300 after exiting the lumen 390 and before attaching to the tension control member 230 (indicated at site "W1"). Conversely, the second tension member 220 extends in a clockwise direction after exiting the lumen 390 and before attaching to the tension control member 230 (indicated at site "W2").

Rotating the tension control member 230 in a clockwise direction causes a pull on the second tension member 220 and a relaxation of the pull on the tension member 210, thus expanding the dilating member 100. Conversely, rotating the tension control member 230 in a counterclockwise direction causes a pull on the tension member 210 and a relaxation of the pull on the second tension member 220, thus collapsing the dilating member 100.

As depicted in FIG. 6a, the tension member 210 exits the lumen 390 via an aperture 320 in a wall of the elongate member 300 while the second tension member 220 exits the lumen 390 at the proximal end 330 of the elongate member 300. In other embodiments, the tension members 210, 220 both exit the lumen 390 at the proximal end 330, through an aperture 320 or exit through more than one aperture 320 disposed near the proximal end 330.

Figure 7A:
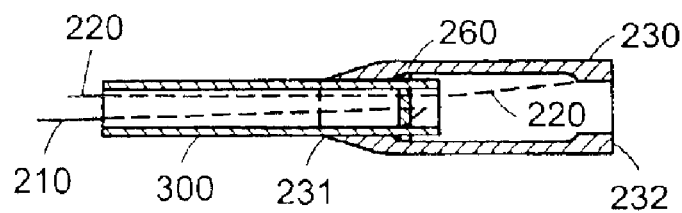
FIG. 7a–c are cutaway views that illustrate use of an embodiment of a tension control member.

Referring to FIG. 7, a tension control member 230 corresponding to FIG. 6a is shown in more detail. FIG. 7a shows the tension control member 230 positioned to hold the dilating member 100 in a collapsed state. The physician has extended the tension control member 230 fully in the distal direction. In the embodiment of FIG. 7, the tension control member 230 has a smaller internal radius near its proximal end 232 and distal end 231 than near its central portion. This permits a frictional fit when positioned fully in a proximal or distal direction. The frictional fit can be assisted, for example, by an elongate member 300 that has a wider portion near or adjacent to its distal end 330. Hence, the tension control member 230 further acts as a locking member to lock the position of the tension members 210, 220 and thus lock the state of the dilating member 100. An o-ring 260 can assist frictional locking, and help to prevent leakage of fluids from the catheter.

Figure 7B:
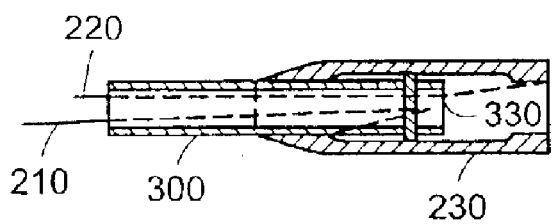
Figure 7C:
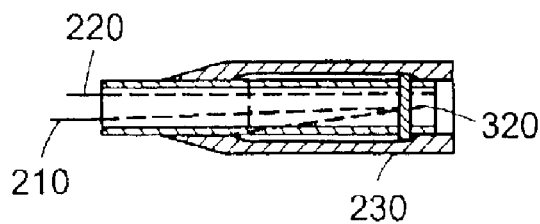

Referring to FIG. 7b, the tension control member 230 is shown in an intermediate position. FIG. 7c is a schematic diagram of the tension control member 230 positioned to hold the dilating member 100 in an expanded state. The physician has moved the tension control member 230 fully in the proximal direction.

Other embodiments include one or more differently configured tension control members 230. For example, the tension control member 230 can be rotatably coupled to the elongate member 300. Movement in clockwise and counterclockwise directions serves to alternately expand and collapse the dilating member 100. In one alternative embodiment, rotation of the tension control member 230 causes one tension member 210, 220 to wind around one spool while the other tension member 210, 220 unwinds around another spool. In another embodiment, rotation of the tension control member 230 causes one tension member 210, 220 to slide against and wrap around the elongate member 300 while the other tension member 210, 220 slides against and unwraps around the elongate member 300.

Referring to FIGS. 8–16, various locking mechanisms can be used to adjust the tension in and lock the positions of one or more threads in a drainage catheter. The locking mechanisms can include a member or portion that is attached to one or more threads that exit the lumen 390 at the proximal end 330 of the elongate member 300, or exit the lumen 390 via one or more an aperture 320 in the wall of the elongate member 300. Movement of the member or portion permits an increase or a decrease in the tension of a thread.

Figure 8:
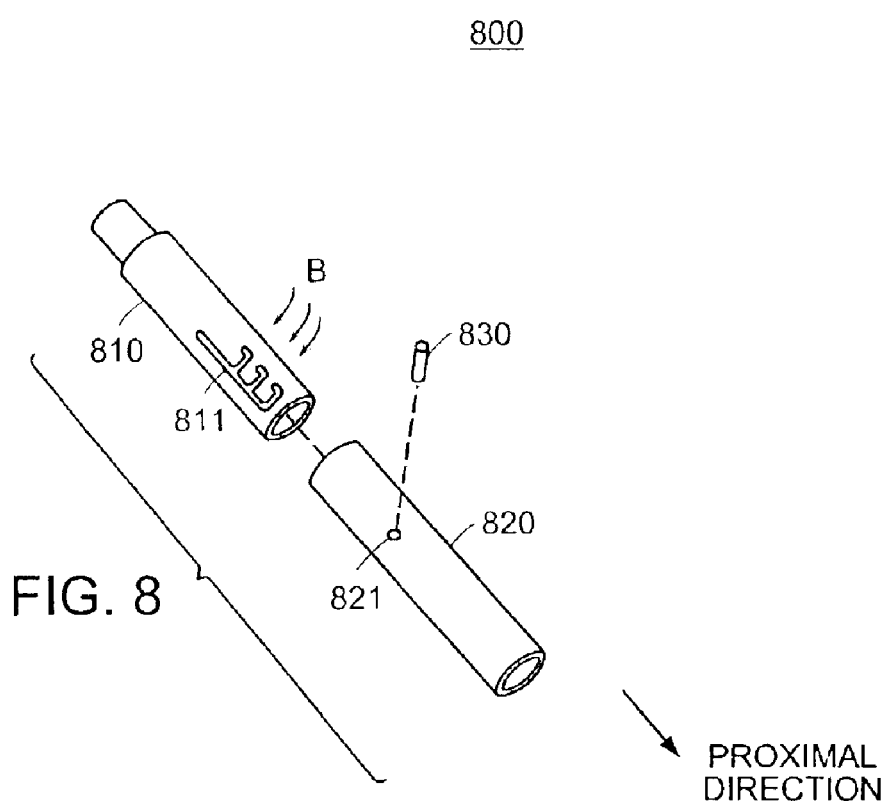
FIG. 8 is a three-dimensional view of an embodiment of a lock member that includes a slotted portion.

FIG. 8. illustrates an embodiment of a lock member 800. The lock member 800 comprises a slotted portion 810 that attaches to the proximal end 330 of the elongate member 300. The slotted portion 810 defines slots 811 that extends through a wall of the slotted portion 810. A housing 820 is disposed around the slotted portion 810. A pin 830 extends inwardly through an aperture 821 in the housing 820 and into the slots 811 to secure the position of the housing 820 relative to the position of the slotted portion 810. One or more tension members 210, 220 are attached to the housing 820. Hence, moving the housing 820 along the longitudinal axis of the elongate member 300 (not shown) can be used to increase or decrease the tension of a tension member 210 or 220.

After positioning the housing 820 for a desired level of tension, the physician inserts the pin 830 through the aperture 821 into one of a set of predefined locations (indicated by "B") in the slots 811. The embodiment depicted in FIG. 8 has pin 830 locations for three different levels of tension. Other embodiments include slots 811 with fewer or more tensioning levels.

Figure 9A:
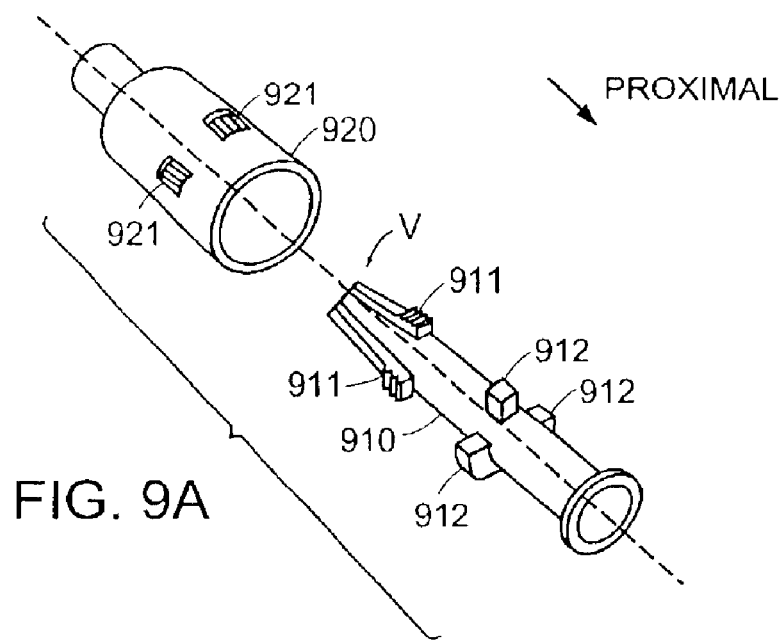
FIG. 9a is a three-dimensional view of an embodiment of a lock member that includes a sliding portion.
Figure 9B:
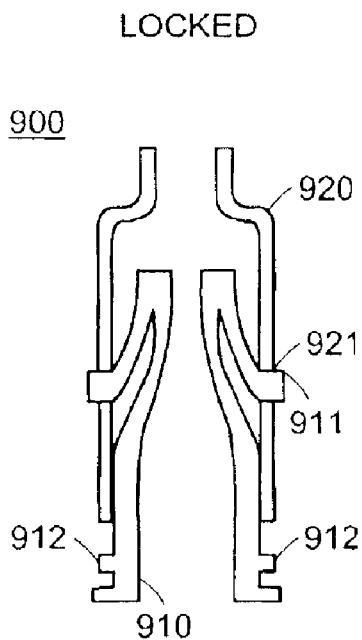
FIG. 9b is a cross-sectional view of the embodiment of FIG. 9a in a locked state.
Figure 9C:
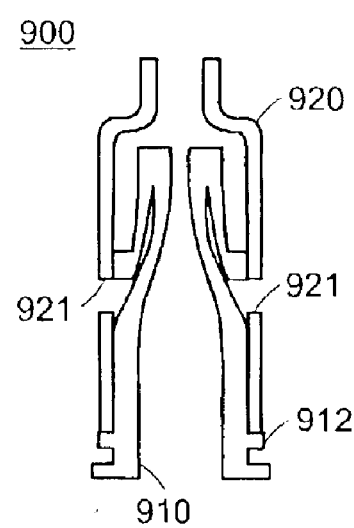
FIG. 9c is a cross-sectional view of the embodiment of FIG. 9a in an unlocked state.

Referring to FIGS. 9a–c, an embodiment of a lock member 900 is shown. FIG. 9a shows a three-dimensional view of the lock member 900, while FIGS. 9b–c are cross-sectional views of the lock member 900 in locked and unlocked states. A housing 920 couples to the proximal end 330 of the elongate member 300. The housing has one or more cutouts 921. A sliding portion 910 fits within the housing 920 and couples to one or more threads. A thread can attach to the sliding portion 910 at various locations (for example, indicated by "V"). The sliding portion has one or more spring portions 911 that can engage with the cutouts 921. By pressing on the spring portions 911 through the cutouts 921, a physician can disengage the spring portions 911 from the cutouts 921, to permit sliding of the sliding portion 910 in a distal direction. In this embodiment, the sliding portion includes stops 912 that limit the travel of the sliding portion 910 in the distal direction.

Figure 10A:
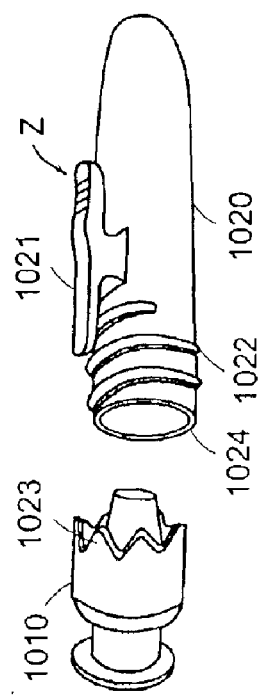
FIG. 10a is a three-dimensional view of an embodiment of a lock member.
Figure 10B:
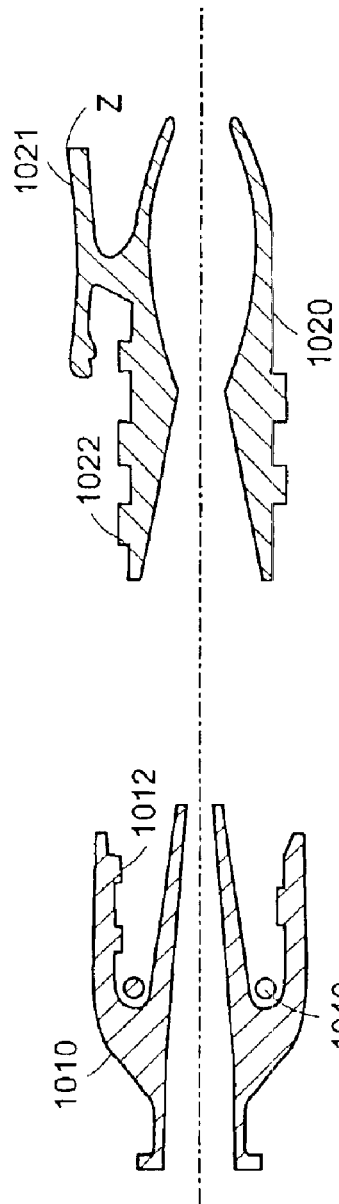

Referring to FIGS. 10a–b, an embodiment of a Luer lock-based lock member 1000 is shown. FIG. 10a shows a three-dimensional view of the lock member 1000, while FIG. 10b is a corresponding cross-sectional view of the lock member 1000. A female fitting 1020 couples to the proximal end 330 of the elongate member 300. A male fitting 1010 has threads 1012 that engage corresponding threads 1022 included in the female fitting 1020. The female fitting 1020 includes a spring ratchet 1021 that engages teeth 1023 included in the male fitting 1010 to lock the rotational position of the male fitting 1010 relative to the female fitting 1020. Pressing on an end (site indicated by "Z") of the ratchet 1021 disengages the ratchet from the teeth 1023 to permit removal of the male fitting 1010 from the female fitting 1020.

The lock member 1000 further includes an o-ring 1040 seated within the male fitting 1010. A proximal end 1024 of the female fitting 1020 presses against the o-ring 1040 when a physician attaches the fittings 1010, 1020. The o-ring 1040 helps to prevent leakage from the catheter and can further help to secure the position of one or more suture threads 210, 220. Other embodiments use other sealing members in place of an o-ring 1040, for example a washer or a grommet.

One can use the lock member 1000 in combination with one or more tension member threads. In one embodiment, the physician simply screws the male fitting 1010 onto the female fitting 1020 after positioning one or more threads with the desired level of tension. In another embodiment, a thread may pass along one side of or through the o-ring 1040 and then exits the male fitting 1010 through an eyelet on the proximal side of the o-ring 1040. In another embodiment, the male fitting 1010 may include an eyelet through which a thread passes into a lumen of the male fitting 1010. In other embodiments, one or more eyelets may be variously positioned in the male fitting 1010 or the female fitting 1020.

Figure 11:
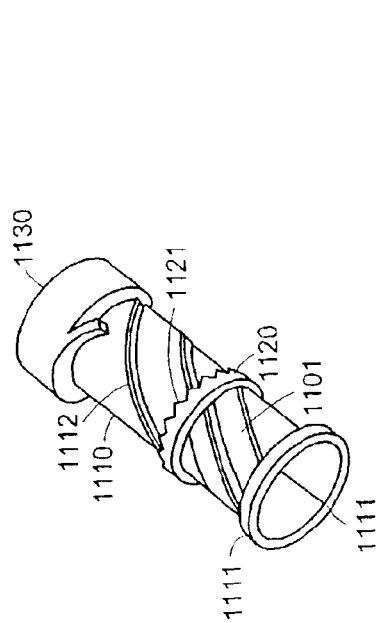
FIG. 11 is a three-dimensional view of an embodiment of a lock member that includes a ring portion.

Referring to FIG. 11, another embodiment of a lock member 1100 is shown. The lock member 1100 includes a grooved portion 1110 fixedly attached to the elongate member 300. The outer surface of the grooved portion 1110 includes a spiral grove 1112. A ring portion 1120 is disposed around the grooved portion 1110 and attached to a tension member comprising a thread 1101. The ring portion 1120 engages a groove 1112 in the grooved portion 1110 that guides the ring portion 1120 in a distal direction as a physician rotates the ring portion 1120 around the grooved portion 1110. As the ring portion 1120 moves in the distal direction, it pulls the thread 1101 through eyelets 1111 in the grooved portion 1110, causing an increase in tension in the thread 1101.

As the ring portion 1120 moves in the distal direction, it eventually contacts a ratchet portion 1130 disposed adjacent to the proximal end 330 of the elongate member 300. The ratchet portion 1130 engages teeth 1121 in the ring portion 1120 to secure the position of the thread 1101. The ratchet portion 1130 also permits variably securing the position of the thread 1101.

Figure 12:
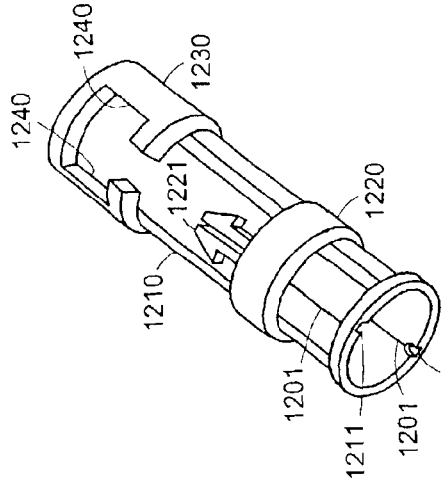
FIG. 12 is a three-dimensional view of an embodiment of a lock member that includes a sliding portion.

Referring to FIG. 12, another embodiment of a lock member 1200 is shown. The lock member 1200 includes a tube portion 1210 fixedly attached to the elongate member 300. A sliding portion 1220 is disposed around the tube portion 1210 and attached to a thread 1201. A physician slides the sliding portion 1220 along the tube portion 1210 to increase the tension in the thread 1201. As the sliding portion 1220 moves in the distal direction, it pulls the thread 1201 through eyelets 1211 in the tube portion 1210, causing an increase in tension in the thread 1201.

As the sliding portion 1220 moves in the distal direction, it eventually contacts a notched portion 1230 disposed adjacent to the proximal end 330 of the elongate member 300. The notched portion 1230 has two opposing notches 1240 engaging flexible teeth 1221 that extend in a distal direction from the sliding portion 1220 to secure the position of the thread 1201 in a tensed position.

Figure 13:
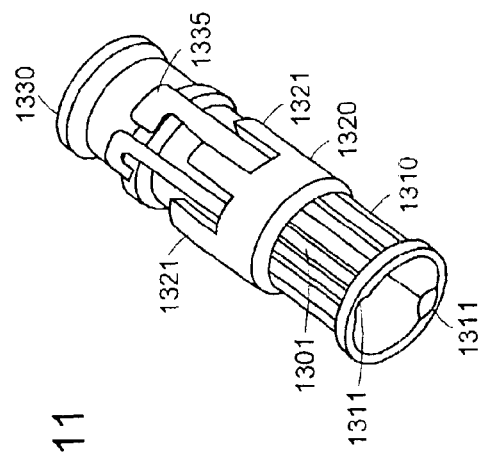
FIG. 13 is a three-dimensional view of an embodiment of a lock member that includes a sliding portion.

Referring to FIG. 13, another embodiment of a lock member 1300 is shown. The lock member 1300 includes a tube portion 1310 attached to the elongate member 300. A sliding portion 1320 is disposed around the tube portion 1310 and attached to a thread 1301. A physician slides the sliding portion 1320 along the tube portion 1310 to increase the tension in the thread 1301. As the sliding portion 1320 moves in the distal direction, it pulls the thread 1301 through eyelets 1311 in the tube portion 1310, causing an increase in tension in the thread 1301.

As the sliding portion 1320 moves in the distal direction, it eventually contacts a notched portion 1330 disposed adjacent to the proximal end 330 of the elongate member 300. The notched portion 1330 has a plurality of notches 1335 that engage a plurality of extensions 1321 that extend in a distal direction from the sliding portion 1320 to secure the position of the thread 1301. The physician slightly rotates the sliding portion 1320 so that the extensions 1321 can engage recesses (indicated by "R") in the notches 1335 by permitting the sliding portion 1320 to return slightly in the proximal direction.

Figure 14:
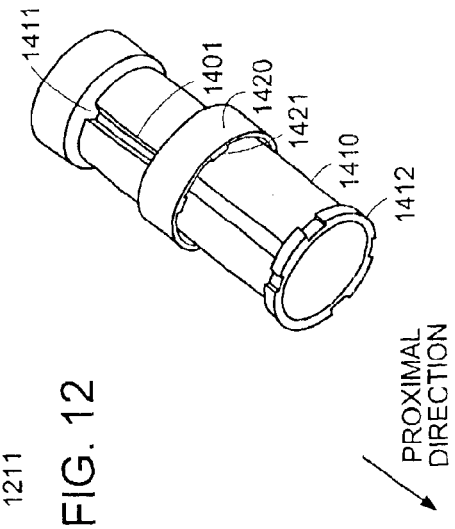
FIG. 14 is a three-dimensional view of an embodiment of a lock member that includes a sliding portion.

Referring to FIG. 14, another embodiment of a lock member 1400 is shown. The embodiment of FIG. 14 is similar in configuration to the embodiment of FIG. 13. Here, however, a physician moves a sliding portion 1420 in a proximal direction along a tube portion 1410 to increase tension in a thread 1401. As the sliding portion 1420 moves in the proximal direction, it pulls the thread 1401 through eyelets 1412 in the tube portion 1410, causing an increase in tension in the thread 1401. Extensions 1421 in the sliding portion 1420 engage teeth 1412 disposed at the proximal end of the tube portion 1410 to secure the position of the thread 1401.

Figure 15:
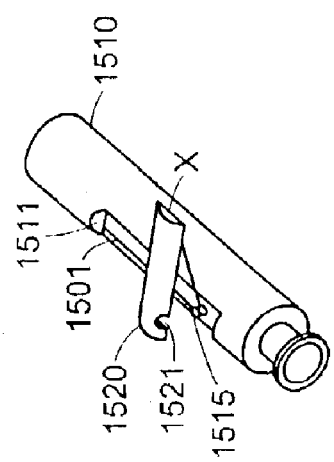
FIG. 15 is a three-dimensional view of an embodiment of a lock member that includes a pivoting member.

Referring to FIG. 15, still another embodiment of a lock member 1500 is shown. A support portion 1510 is disposed at the proximal end 330 of the elongate member 300. A pivoting portion 1520 is pivotally attached to the support portion 1510. A thread 1501 passes from the lumen 390 of the elongate member 300 through an eyelet 1511 in the support portion 1510 and attaches to one end (indicated by "X") of the pivoting portion 1520.

When a physician or other medical worker rotates the pivoting portion 1520 around an axis perpendicular to the longitudinal axis of the elongate member 300, the rotating member either pulls on or releases the pull on the thread 1501. Hence, the tension in the thread 1510 is increased or reduced, depending on the direction of rotation. The support portion 1510 further includes a pivot extension 1515 around which the thread 1501 slides. The pivot extension 1515 further engages a notch 1521 in the pivoting portion 1520 to secure the position of the pivoting portion 1520. Other embodiments include more than one pivoting portion 1520 for control of additional threads 1501.

Figure 16:
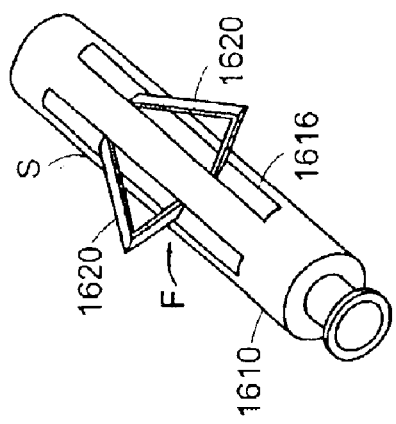
FIG. 16 is a three-dimensional view of an embodiment of a lock member that includes a folding member.

Referring to FIG. 16, another embodiment of a lock member 1600 is shown. The lock member 1600 includes a support member 1610 disposed at the proximal end 330 of the elongate member 300 (not shown). One or more folding members 1620 are foldably attached to the support member 1610.

One end of each folding member 1620 is coupled to the support member 1610 at a fixed location (indicated by "F"). The coupling comprises a folding joint, for example a hinge joint. The opposite end of the folding member 1620 is slidably coupled to the support member 1610 (indicated by "S").

As the folding member 1620 is folded, the slidably coupled end slides toward the fixed location end of the folding member 1620. When completely folded, the folding member 1620 lies flat against the support member 1610, and resides in a recess 1616 in the surface of the support member 1610. A thread (not shown) can be attached at various sites along the folding member 1620 to allow a pull or a release of the thread when the folding member 1620 is folded.

Figure 17:
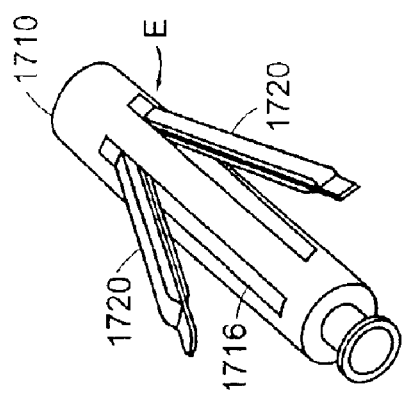
FIG. 17 is a three-dimensional view of an embodiment of a lock member that includes a flipping member.

Referring to FIG. 17, another embodiment of a lock member 1700 is shown. The lock member 1700 includes a support member 1710 disposed at the proximal end 330 of the elongate member 300. One or more flipping members 1720 are flippably attached to the support member 1710.

One end of each flipping member 1720 is coupled to the support member 1710 (indicated by "E"). The coupling permits the flipping member 1720 simultaneously to slide and rotate by 180°, i.e. flip, relative to the support member 1710.

When lying flat against the support member 1710, the flipping member 1720 resides within a recess 1716 in the surface of the support member 1710. A thread (not shown) can be attached to various sites along the flipping member 1720 to allow a pull or a release of the thread when the flipping member 1720 is folded.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

What is claimed is:

1. A medical device, the device comprising:
   an elongate member;
   a dilating member disposed in a distal portion of the elongate member and movable from a collapsed state to an expanded state to anchor the device within a body;
   a first tension member coupled to the dilating member such that an application of tension to the first tension member causes the dilating member to move to the collapsed state thereby permitting removal of the device from the body;
   a second tension member coupled to the dilating member such that an application of tension to the second tension member causes the dilating member to move to the expanded state; and
   a tension control member coupled to the first tension member and the second tension member.

2. The device of claim 1, wherein the tension control member is movable in at least a first direction and a second direction and is coupled to the first and second tension members such that movement of the tension control member in the first direction causes an increase in tension of the first tension member and a decrease in tension of the second tension member that causes the dilating member to move to the collapsed state, and such that movement of the tension control member in the second direction causes an increase in tension of the second tension member and a decrease in tension of the first tension member that causes the dilating member to move to the expanded state.

3. The device of claim 1, wherein the tension control member is slidably coupled to the elongate member.

4. The device of claim 1, wherein the tension control member is rotatably coupled to the elongate member.

5. The device of claim 1, wherein the tension control member is lockable to fix the tensions in the tension members.

6. The device of claim 5, wherein the tension control member comprises a pivoting portion attached to the tension member.

7. The device of claim 5, wherein the tension control member comprises a folding member attached to the tension member.

8. The device of claim 5, wherein the tension control member comprises a flipping member attached to the tension member.

9. The device of claim 1, wherein the distal portion includes an extension on a distal end of the dilating member.

10. The device of claim 1, wherein the distal portion terminates at a distal end of the dilating member.

11. The device of claim 1, wherein the dilating member comprises a plurality of arms.

12. The device of claim 1, wherein the plurality of arms protrude radially when the dilating member is in the expanded state.

13. The device of claim 1, further comprising a lock member to secure a position of the tension member when the dilating member is in the collapsed state.

14. The device of claim 13, wherein the tension member is secured by compression between the lock member and the elongate member.

15. The device of claim 1, wherein the tension member is formed from a bio-compatible thread.

16. A medical device, the device comprising:
   an elongate member;
   a dilating member disposed in a distal portion of the elongate member and movable from a collapsed state to an expanded state to anchor the device within a body;
   a first tension member coupled to the dilating member;
   a second tension member coupled to the dilating member; and
   a tension control member movable in at least a first direction and a second direction,
   wherein the tension control member is coupled to the first and second tension members such that movement of the tension control member in the first direction causes an increase in tension of the first tension member and a decrease in tension of the second tension member that causes the dilating member to move to the collapsed state thereby permitting removal of the device from the body, and such that movement of the tension control member in the second direction causes an increase in tension of the second tension member and a decrease in tension of the first tension member that causes the dilating member to move to the expanded state, and
   wherein the tension control member is lockable to fix the tensions of the tension members, and
   wherein the tension control member is selected from the group consisting of a pivoting portion attached to the tension members, a folding member attached to the tension members, and a flipping member attached to the tension members.

* * * * *